US009962541B2

(12) United States Patent
Howard et al.

(10) Patent No.: US 9,962,541 B2
(45) Date of Patent: May 8, 2018

(54) LEADS WITH ELECTRODE CARRIERS FOR SEGMENTED ELECTRODES AND METHODS OF MAKING AND USING

(71) Applicant: Boston Scientific Neuromodulation Corporation, Valencia, CA (US)

(72) Inventors: Joshua Dale Howard, Winnetka, CA (US); James Robert Black, Medina, OH (US); Jose Ulloa, Valencia, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

(21) Appl. No.: 14/738,494

(22) Filed: Jun. 12, 2015

(65) Prior Publication Data

US 2015/0360023 A1 Dec. 17, 2015

Related U.S. Application Data

(60) Provisional application No. 62/012,166, filed on Jun. 13, 2014.

(51) Int. Cl.
*A61N 1/00* (2006.01)
*A61N 1/05* (2006.01)

(52) U.S. Cl.
CPC ............. *A61N 1/0534* (2013.01); *A61N 1/05* (2013.01); *A61N 1/0529* (2013.01); *Y10T 29/49171* (2015.01)

(58) Field of Classification Search
CPC ................................ A61N 1/0534; A61N 1/05
(Continued)

(56) References Cited

U.S. PATENT DOCUMENTS 4,602,624 A 7/1986 Naples et al.
4,630,611 A 12/1986 King
(Continued)

FOREIGN PATENT DOCUMENTS

EP 0580928 A1 2/1994
EP 0650694 B1 7/1998
(Continued)

OTHER PUBLICATIONS

International Search Report and Written Opinion for PCT Application No. PCT/US2015/035632 dated Aug. 11, 2015.

*Primary Examiner* — Nadia A Mahmood
(74) *Attorney, Agent, or Firm* — Lowe Graham Jones PLLC; Bruce E. Black

(57) ABSTRACT

A stimulation lead includes an electrode carrier disposed along a distal portion of a lead body. The electrode carrier defines multiple segmented-electrode-receiving apertures extending between an outer surface and a central lumen. Each of the segmented-electrode-receiving apertures includes a ledge disposed around a perimeter of that segmented-electrode-receiving aperture and inset from the outer surface of the electrode carrier. The stimulation lead also includes multiple segmented electrodes, with each of the segmented electrode disposed in a different one of the segmented-electrode-receiving apertures with an outer stimulation surface exposed through the segmented-electrode-receiving aperture and an inner surface abutting the ledge disposed around the perimeter of that segmented-electrode-receiving aperture. Conductive wires extend along the lead body and couple the segmented electrodes to terminals.

11 Claims, 10 Drawing Sheets

(58) Field of Classification Search
USPC .................................................. 607/115, 116
See application file for complete search history.

(56) References Cited

U.S. PATENT DOCUMENTS

| | | | |
|---|---|---|---|
| 4,744,370 | A | 5/1988 | Harris |
| 5,000,194 | A | 3/1991 | van den Honert et al. |
| 5,135,001 | A | 8/1992 | Sinofsky et al. |
| 5,374,285 | A | 12/1994 | Vaiani et al. |
| 5,458,629 | A | 10/1995 | Baudino et al. |
| 5,522,874 | A | 6/1996 | Gates |
| 5,711,316 | A | 1/1998 | Elsberry et al. |
| 5,713,922 | A | 2/1998 | King |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,134,478 | A | 10/2000 | Spehr |
| 6,161,047 | A | 12/2000 | King et al. |
| 6,167,311 | A | 12/2000 | Rezai |
| 6,181,969 | B1 | 1/2001 | Gord |
| 6,322,559 | B1 | 11/2001 | Daulton et al. |
| 6,510,347 | B2 | 1/2003 | Borkan |
| 6,516,227 | B1 | 2/2003 | Meadows et al. |
| 6,556,873 | B1 | 4/2003 | Smits |
| 6,564,078 | B1 | 5/2003 | Marino et al. |
| 6,609,029 | B1 | 8/2003 | Mann et al. |
| 6,609,032 | B1 | 8/2003 | Woods et al. |
| 6,678,564 | B2 | 1/2004 | Ketterl et al. |
| 6,741,892 | B1 | 5/2004 | Meadows et al. |
| 6,757,970 | B1 | 7/2004 | Kuzma et al. |
| 7,027,852 | B2 | 4/2006 | Helland |
| 7,047,084 | B2 | 5/2006 | Erickson et al. |
| 7,203,548 | B2 | 4/2007 | Whitehurst et al. |
| 7,244,150 | B1 | 7/2007 | Brase et al. |
| 7,292,890 | B2 | 11/2007 | Whitehurst et al. |
| 7,450,997 | B1 | 11/2008 | Pianca et al. |
| 7,489,971 | B1 | 2/2009 | Franz |
| 7,668,601 | B2 | 2/2010 | Hegland et al. |
| 7,672,734 | B2 | 3/2010 | Anderson et al. |
| 7,761,165 | B1 | 7/2010 | He et al. |
| 7,761,985 | B2 | 7/2010 | Hegland et al. |
| 7,783,359 | B2 | 8/2010 | Meadows |
| 7,792,590 | B1 | 9/2010 | Pianca et al. |
| 7,809,446 | B2 | 10/2010 | Meadows |
| 7,822,482 | B2 | 10/2010 | Gerber |
| 7,840,188 | B2 | 11/2010 | Kurokawa |
| 7,848,802 | B2 | 12/2010 | Goetz |
| 7,856,707 | B2 | 12/2010 | Cole |
| 7,860,570 | B2 | 12/2010 | Whitehurst et al. |
| 7,949,395 | B2 | 5/2011 | Kuzma |
| 7,974,705 | B2 | 7/2011 | Zdeblick et al. |
| 7,974,706 | B2 | 7/2011 | Moffitt et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,099,177 | B2 | 1/2012 | Dahlberg |
| 8,175,710 | B2 | 5/2012 | He |
| 8,224,450 | B2 | 7/2012 | Brase |
| 8,225,504 | B2 | 7/2012 | Dye et al. |
| 8,271,094 | B1 | 9/2012 | Moffitt et al. |
| 8,295,944 | B2 | 10/2012 | Howard et al. |
| 8,321,025 | B2 | 11/2012 | Bedenbaugh |
| 8,359,107 | B2 | 1/2013 | Pianca et al. |
| 8,364,278 | B2 | 1/2013 | Pianca et al. |
| 8,391,985 | B2 | 3/2013 | McDonald |
| 8,583,237 | B2 | 11/2013 | Bedenbaugh |
| 8,688,235 | B1 | 4/2014 | Pianca et al. |
| 2001/0023368 | A1 | 9/2001 | Black et al. |
| 2002/0156513 | A1 | 10/2002 | Borkan |
| 2002/0183817 | A1 | 12/2002 | Van Venrooij et al. |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0247697 | A1 | 11/2006 | Sharma et al. |
| 2007/0150036 | A1 | 6/2007 | Anderson |
| 2007/0168007 | A1 | 7/2007 | Kuzma et al. |
| 2007/0203546 | A1 | 8/2007 | Stone et al. |
| 2007/0219551 | A1 | 9/2007 | Honour et al. |
| 2008/0046049 | A1 | 2/2008 | Skubitz et al. |
| 2008/0077186 | A1 | 3/2008 | Thompson et al. |
| 2008/0103580 | A1 | 5/2008 | Gerber |
| 2008/0114230 | A1 | 5/2008 | Addis |
| 2008/0200972 | A1 | 8/2008 | Rittman et al. |
| 2008/0215125 | A1 | 9/2008 | Farah et al. |
| 2008/0255647 | A1 | 10/2008 | Jensen et al. |
| 2009/0054941 | A1 | 2/2009 | Eggen et al. |
| 2009/0187222 | A1 | 7/2009 | Barker |
| 2009/0204192 | A1 | 8/2009 | Carlton et al. |
| 2009/0276021 | A1 | 11/2009 | Meadows et al. |
| 2010/0030298 | A1 | 2/2010 | Martens et al. |
| 2010/0036468 | A1 | 2/2010 | Decre et al. |
| 2010/0076535 | A1 | 3/2010 | Pianca et al. |
| 2010/0077606 | A1 | 4/2010 | Black et al. |
| 2010/0082076 | A1 | 4/2010 | Lee et al. |
| 2010/0094387 | A1 | 4/2010 | Pianca et al. |
| 2010/0100152 | A1 | 4/2010 | Martens et al. |
| 2010/0268298 | A1 | 10/2010 | Moffitt et al. |
| 2010/0269338 | A1 | 10/2010 | Dye |
| 2010/0269339 | A1 | 10/2010 | Dye et al. |
| 2010/0287770 | A1 | 11/2010 | Dadd et al. |
| 2011/0004267 | A1 | 1/2011 | Meadows |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0072659 | A1 | 3/2011 | Swanson et al. |
| 2011/0077699 | A1 | 3/2011 | Swanson et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0245903 | A1* | 10/2011 | Schulte ............ A61N 1/0534 607/115 |
| 2011/0301665 | A1 | 12/2011 | Mercanzini et al. |
| 2011/0313500 | A1* | 12/2011 | Barker ............ A61N 1/0534 607/116 |
| 2012/0016378 | A1 | 1/2012 | Pianca et al. |
| 2012/0046710 | A1 | 2/2012 | DiGiore et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | DiGiore et al. |
| 2012/0203321 | A1 | 8/2012 | Moffitt et al. |
| 2012/0316615 | A1 | 12/2012 | DiGiore et al. |
| 2013/0105071 | A1 | 5/2013 | DiGiore et al. |
| 2013/0109254 | A1 | 5/2013 | Klardie et al. |
| 2013/0197424 | A1 | 8/2013 | Bedenbaugh |
| 2013/0197602 | A1 | 8/2013 | Pianca et al. |
| 2013/0261684 | A1 | 10/2013 | Howard |
| 2013/0317583 | A1 | 11/2013 | Pianca |
| 2013/0317585 | A1 | 11/2013 | Barker |
| 2013/0317586 | A1 | 11/2013 | Pianca |
| 2013/0317587 | A1 | 11/2013 | Barker |
| 2013/0317588 | A1 | 11/2013 | Howard et al. |
| 2013/0325091 | A1 | 12/2013 | Pianca et al. |
| 2014/0039587 | A1* | 2/2014 | Romero ............ A61N 1/0556 607/116 |
| 2014/0088666 | A1 | 3/2014 | Goetz et al. |
| 2014/0142671 | A1 | 5/2014 | Moffitt et al. |
| 2014/0180375 | A1 | 6/2014 | Pianca et al. |
| 2014/0353001 | A1 | 12/2014 | Romero et al. |
| 2014/0358207 | A1 | 12/2014 | Romero |
| 2014/0358208 | A1 | 12/2014 | Howard et al. |
| 2014/0358209 | A1 | 12/2014 | Romero et al. |
| 2014/0358210 | A1 | 12/2014 | Howard et al. |
| 2015/0018915 | A1 | 1/2015 | Leven |

(56) References Cited

U.S. PATENT DOCUMENTS

| | | |
|---|---|---|
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

* cited by examiner

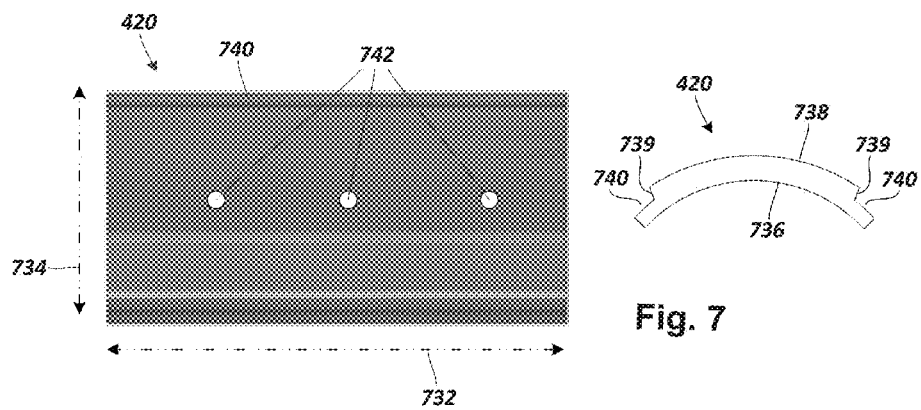
Fig. 7
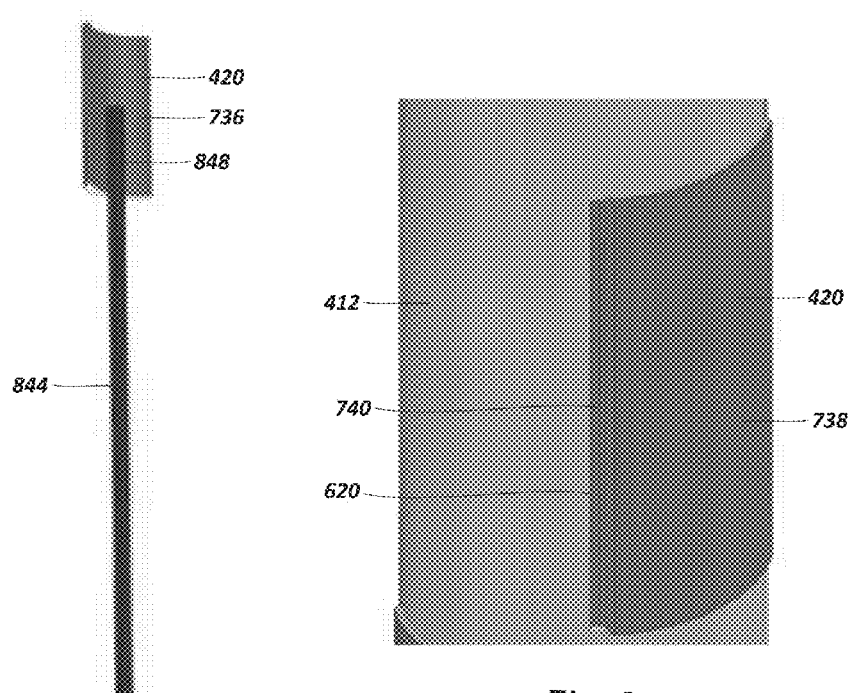
Fig. 8
Fig. 9

LEADS WITH ELECTRODE CARRIERS FOR SEGMENTED ELECTRODES AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/012,166, filed Jun. 13, 2014, which is incorporated herein by reference.

FIELD

The invention is directed to the area of electrical stimulation systems and methods of making and using the systems. The present invention is also directed to electrical stimulation leads with segmented electrodes that can be used for directed electrical stimulation, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead that includes a lead body having a longitudinal length, a distal portion, and a proximal portion. Terminals are disposed along the proximal portion of the lead body. An electrode carrier is coupled to, or disposed along, the distal portion of the lead body. The electrode carrier has an outer surface and includes a central lumen and a stimulation region. The stimulation region defines multiple segmented-electrode-receiving apertures extending between the outer surface and the central lumen. The stimulation region is formed of a non-conductive material. For each of the segmented-electrode-receiving apertures, a ledge is disposed around a perimeter of that segmented-electrode-receiving aperture with the ledge inset from the outer surface of the electrode carrier. The stimulation lead also includes multiple electrodes. The multiple electrodes include multiple segmented electrodes each having an outer stimulation surface, an opposing inner surface, and sidewalls connecting the outer stimulation surface to the inner surface. Each of the segmented electrodes extends around no more than 75% of a circumference of the lead. Each of the segmented electrodes is disposed in a different one of the segmented-electrode-receiving apertures of the electrode carrier with the outer stimulation surface exposed through the segmented-electrode-receiving aperture and the inner surface abutting the ledge disposed around the perimeter of that segmented-electrode-receiving aperture. Conductive wires extend along the lead body and couple the electrodes to the terminals.

In at least some embodiments, the lead further includes a conductor carrier disposed along the central lumen of the electrode carrier, where the conductor carrier defines a central lumen, and where the conductor carrier houses portions of each of the conductive wires. In at least some embodiments, the conductor carrier defines conductor lumens disposed peripherally about the central lumen of the conductor carrier, where the conductive wires are disposed in the conductor lumens. In at least some embodiments, the conductor carrier defines an ablated region exposing each of the conductor lumens to the segmented-electrode-receiving apertures.

In at least some embodiments, the electrode carrier includes an inner sleeve and an outer sleeve disposed over the inner sleeve, where the outer sleeve defines the segmented-electrode-receiving apertures and the inner sleeve defines conductor apertures exposing the central lumen of the electrode carrier to the segmented-electrode-receiving apertures defined in the outer sleeve. In at least some embodiments, the outer stimulation surfaces of the segmented electrodes are arc-shaped. In at least some embodiments, at least one of the segmented electrodes defines at least one coupling groove disposed along the outer stimulation surface of the segmented electrode, the at least one coupling groove attached to the stimulation region of the electrode carrier via adhesive. In at least some embodiments, at least one of the segmented electrodes defines at least one anchoring aperture extending between the outer stimulation surface and the inner surface of the segmented electrode, the at least one anchoring aperture filled with polymeric material. In at least some embodiments, at least one of the segmented electrodes includes at least one anchoring tab extending outwardly from at least one of the sidewalls of the segmented electrode. In at least some embodiments, the electrodes further include at least one of a tip electrode or at least one ring electrode.

Another embodiment is an electrical stimulating system that includes the stimulation lead described above, as well as a control module electrically coupled to the electrodes of the lead and a connector assembly for receiving the lead. The control module includes a housing, and an electronic subassembly disposed in the housing. The connector assembly includes a connector housing defining at least one port configured and arranged for receiving the lead, and connector contacts disposed in the connector housing and configured and arranged to couple to the terminals disposed along the proximal portion of the lead.

Yet another embodiment is a method of making a stimulation lead. The method includes providing a non-conductive electrode carrier defining a plurality of segmented-electrode-receiving apertures. For each of the segmented-electrode-receiving apertures, a ledge is disposed around a perimeter of that segmented-electrode-receiving aperture. The ledge is inset from an outer surface of the electrode carrier. Segmented electrodes are pressed into the segmented-electrode-receiving apertures until inner surfaces of the plurality of segmented electrodes abut the inset ledges. Each of the segmented electrodes extends around no more than 75% of a circumference of the lead. Each of the segmented electrodes is disposed in a different one of the segmented-electrode-receiving apertures of the electrode carrier. Conductors are electrically coupled to the segmented electrodes. Conductors are electrically coupled to the terminals disposed along an opposing end of the lead.

In at least some embodiments, the segmented electrodes are retained in the segmented-electrode-receiving apertures by an interference fit. In at least some embodiments, the method further includes applying adhesive to at least one coupling groove defined along an outer stimulation surface of at least one of the segmented electrodes, the adhesive coupling the segmented electrode to the electrode carrier. In at least some embodiments, electrically coupling the conductors to terminals includes extending the conductors along a longitudinal length of a conductor carrier at least partially disposed along a central lumen of the electrode carrier.

In at least some embodiments, extending the conductors along a longitudinal length of the conductor carrier includes extending the conductors through conductor apertures defined along a portion of the conductor carrier. In at least some embodiments, extending the conductors along a longitudinal length of the conductor carrier includes extending the conductors through an ablated region defined along a portion of the conductor carrier.

In at least some embodiments, the method further includes backfilling the electrode carrier with a polymeric material. In at least some embodiments, the method further includes reflowing the electrode carrier with a polymeric material. In at least some embodiments, pressing the segmented electrodes into the segmented-electrode-receiving apertures occurs after electrically coupling a plurality of conductors to the plurality of segmented electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7 is a schematic top view and a schematic end view of one embodiment of a segmented electrode suitable for insertion into one of the segmented-electrode-receiving apertures of the electrode carrier of FIG. 5, according to the invention;

FIG. 8 is a schematic perspective view of one embodiment of a conductor coupled to the segmented electrode of FIG. 7, according to the invention;

FIG. 9 is a schematic perspective view of one embodiment of the segmented electrode of FIG. 7 disposed in one of the segmented-electrode-receiving apertures of the electrode carrier of FIG. 5, according to the invention;

DETAILED DESCRIPTION

The invention is directed to the area of electrical stimulation systems and methods of making and using the systems. The present invention is also directed to electrical stimulation leads with segmented electrodes that can be used for directed electrical stimulation, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

Figure 1:
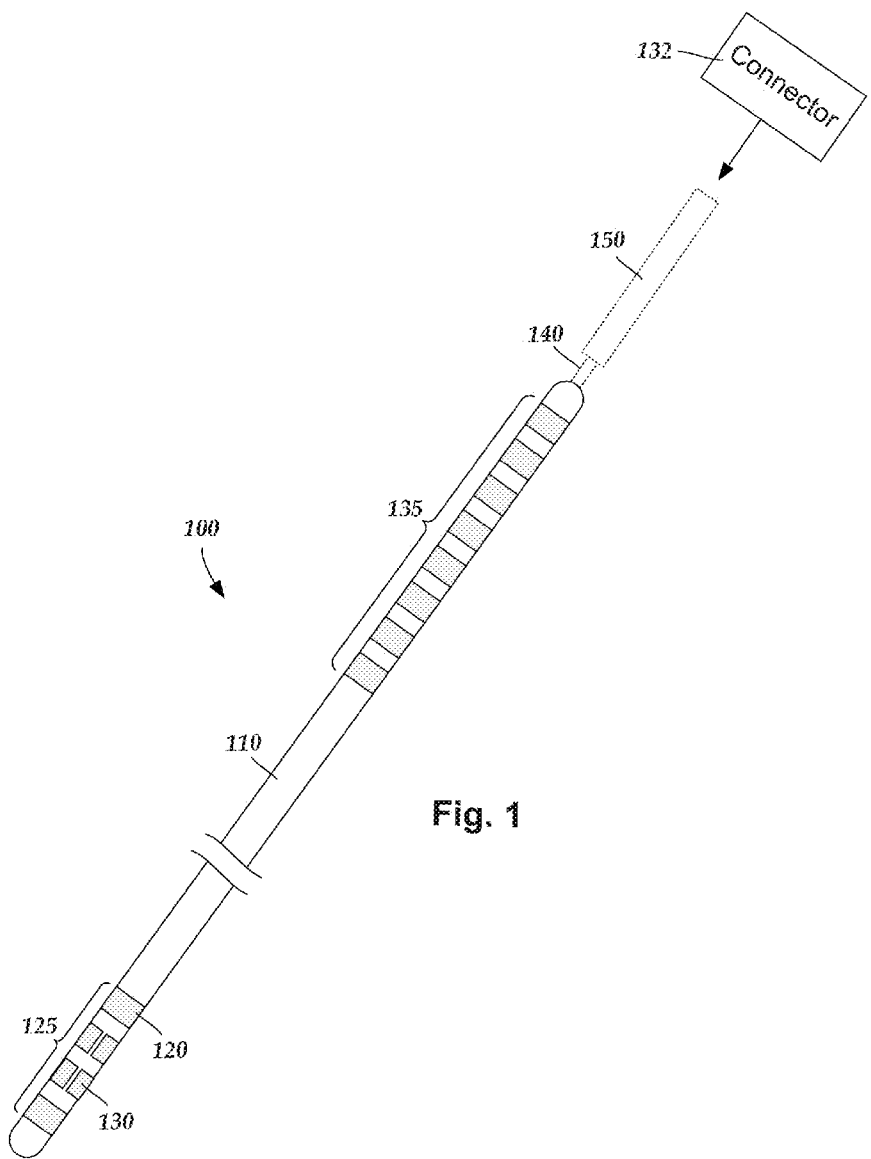
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more or fewer than eight stimulation channels (e.g., 4-, 6-, 16-, 32- or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 1 to 1.5 mm. In at least some embodiments, the lead 100 has a length of at least 10 cm and the length of the lead 100 may be in the range of 15 to 70 cm.

The electrodes may be made using a metal, alloy, conductive oxide, or any other suitable conductive biocompatible material. Examples of suitable materials include, but are not limited to, platinum, platinum iridium alloy, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 may be disposed on any part of the lead body 110, usually near a distal end of the lead 100. In FIG. 1, the lead 100 includes two ring electrodes 120. Any number of ring electrodes 120 may be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes may be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,295,944; and 8,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference.

In FIG. 1, the lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110.

The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two sets of ring electrodes 120 and two sets of segmented electrodes 130, the ring electrodes 120 can flank the two sets of segmented electrodes 130 (see e.g., FIG. 1). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration. It may be useful to refer to the electrodes with this shorthand notation. Thus, the embodiment of FIG. 3C may be referred to as a 4-4-1-1 configuration, while the embodiment of FIG. 3D may be referred to as a 1-1-4-4 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
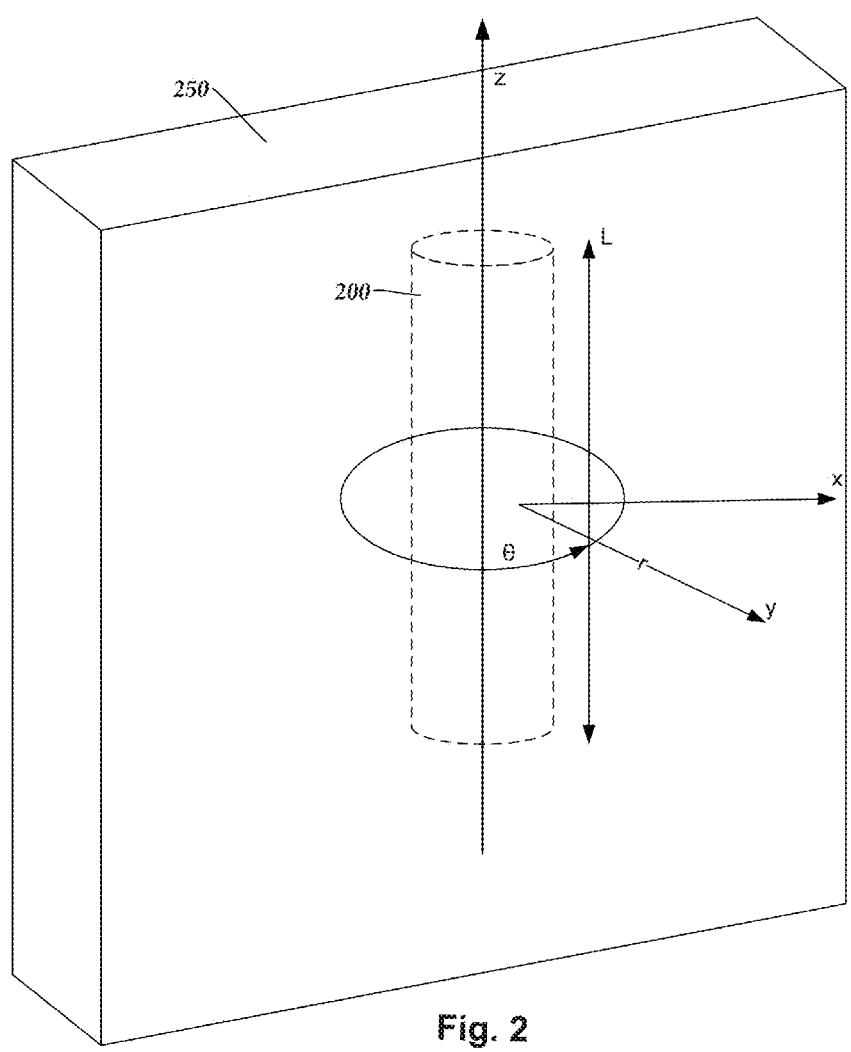
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

Figure 3:
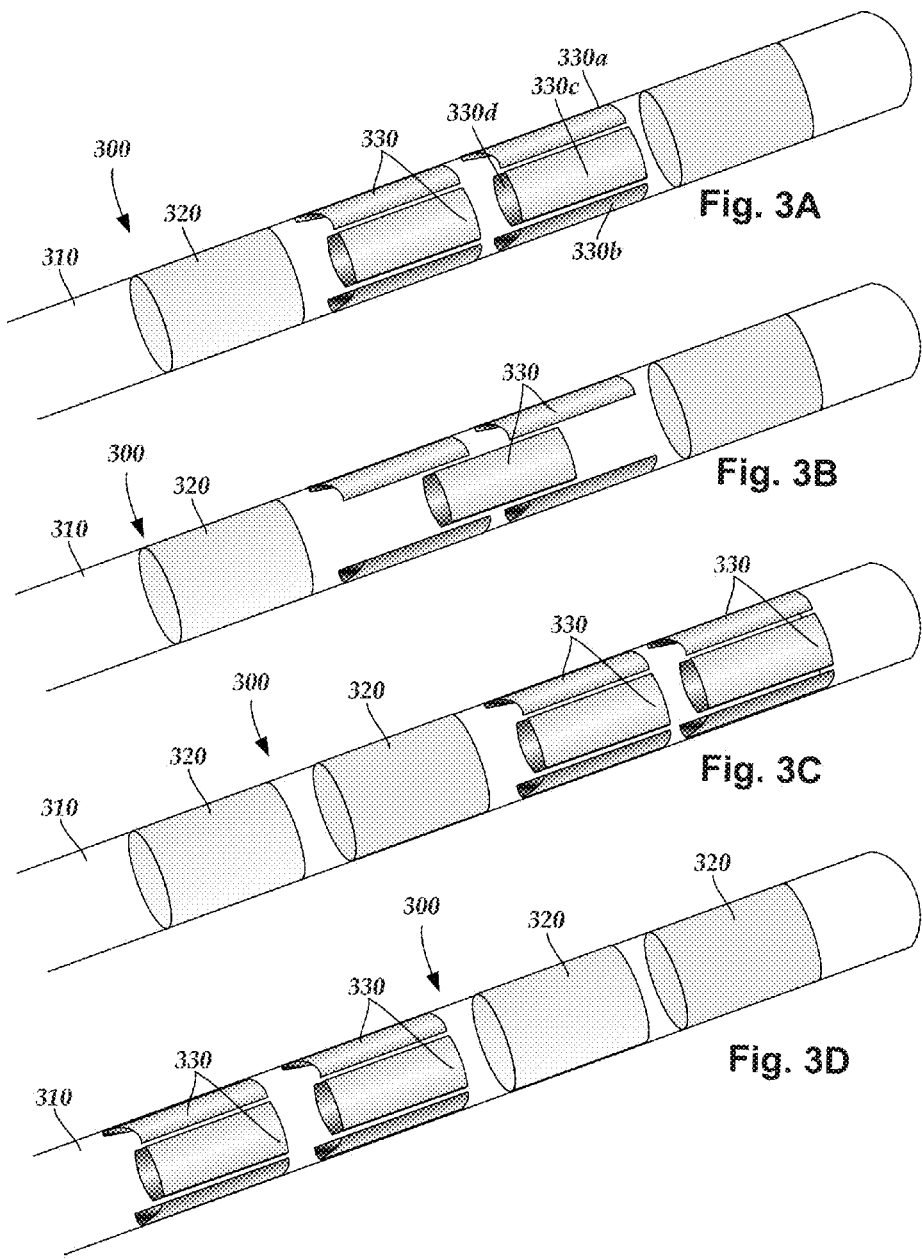
FIG. 3A is a perspective view of an embodiment of a portion of a lead having a plurality of segmented electrodes, according to the invention.
FIG. 3B is a perspective view of a second embodiment of a portion of a lead having a plurality of segmented electrodes, according to the invention.
FIG. 3C is a perspective view of a third embodiment of a portion of a lead having a plurality of segmented electrodes, according to the invention.
FIG. 3D is a perspective view of a fourth embodiment of a portion of a lead having a plurality of segmented electrodes, according to the invention.

In other embodiments, individual electrodes in the two sets of segmented electrodes 130 are staggered (see. FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3D illustrate leads 300 with segmented electrodes 330, optional ring electrodes 320, and a lead body 310. The sets of segmented electrodes 330 include either two (FIG. 3B) or four (FIGS. 3A, 3C, and 3D) or any other number of segmented electrodes including, for example, three, five, six, or more.

Any other suitable arrangements of segmented electrodes can be used. As an example, arrangements in which segmented electrodes are arranged helically with respect to each other. One embodiment includes a single helix. Another embodiment includes a double helix.

Figure 4:
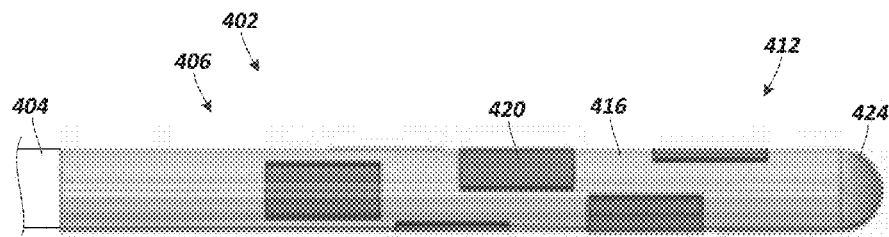
FIG. 4 is a schematic side view of one embodiment of a distal portion of a lead that includes segmented electrodes disposed along an electrode carrier, according to the invention.

Turning to FIG. 4, one challenge to making leads with segmented electrodes is the correct placement of the electrodes, and retention of the desired electrode placement, during the manufacturing process. As herein described, an electrode carrier can be utilized to hold the electrodes in the desired spatial arrangement during the manufacture of the lead. The electrode carrier is made of a non-conductive material to electrically isolate the segmented electrodes from each other and from the one or more ring electrodes (or a tip electrode, or both), if present.

The electrode carrier is described with respect to a deep brain stimulation lead. It will be understood that the electrode carrier can be used in conjunction with other types of leads including, for example, spinal cord stimulation leads, dorsal root ganglia leads, or the like. Examples of spinal cord stimulation leads and dorsal root ganglia leads include U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224.450; and 8,364,278; and U.S. Patent Applications Publication Nos. 2013/0317583; 2013/0317586; 2013/0317585; 2013/0317588; and 2013/0317587, all of which are incorporated herein by reference.

FIG. 4 illustrates, in schematic side view, one embodiment of a distal portion 406 of a lead 402 that includes an electrode carrier 412 disposed along, or coupled to, a body 404 of the lead 402. The electrode carrier 412 includes a stimulation region 416 along which multiple segmented electrodes, such as segmented electrode 420, are exposed. Optionally, the electrode carrier 412 includes a closed distal tip 424.

Figure 5:
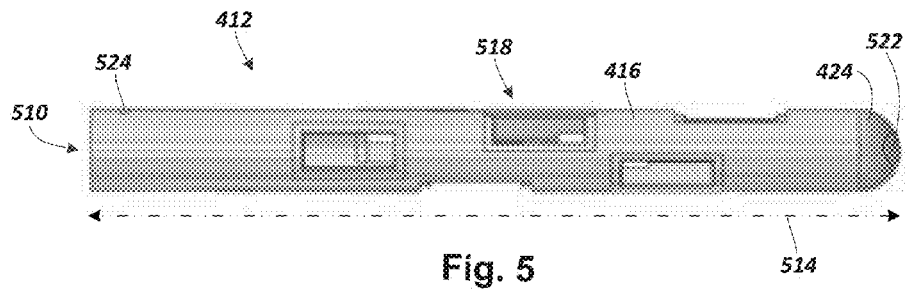
FIG. 5 is a schematic side view of one embodiment of the electrode carrier of FIG. 4, the electrode carrier defining multiple segmented-electrode-receiving apertures for receiving segmented electrodes, according to the invention.

FIG. 5 illustrates, in schematic side view, one embodiment of the electrode carrier 412. The electrode carrier 412 defines a central lumen 510 and has a longitudinal length 514 that extends parallel to a longitudinal length of the lead body 404. Multiple segmented-electrode-receiving apertures, such as segmented-electrode-receiving aperture 518, are defined along the stimulation region 416 of the electrode carrier 412. Each of the segmented-electrode-receiving apertures 518 is suitable for receiving at least one of the segmented electrodes 420. In at least some embodiments, at least one of the segmented-electrode-receiving apertures 518 is suitable for receiving a single segmented electrode 420.

The electrode carrier 412 can be formed from any non-conductive, biocompatible material including, for example, silicone, polyurethane, polyesteresterketone, or the like. The electrode carrier can be formed using any suitable technique including, for example, injection molding. Optionally, one or more injection ports 522 and one or more vent ports 524 are disposed along the electrode carrier 412 for facilitating backfilling of non-conductive material (e.g., epoxy, or the like) into the electrode carrier 412. It will be understood that the optional injection port(s) 522 and vent port(s) 524 can be disposed along any suitable portion of the electrode carrier 412.

Figure 6:
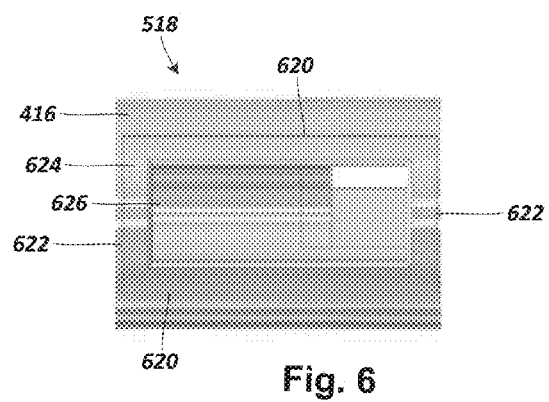
FIG. 6 is a schematic close-up side view of one embodiment of a segmented-electrode-receiving aperture of the electrode carrier of FIG. 5, according to the invention.

FIG. 6 illustrates, in schematic close-up side view, one embodiment of a segmented-electrode-receiving aperture 518 suitable for receiving one of the segmented electrodes 420. The segmented-electrode-receiving aperture 518 can have any suitable shape including, for example, rectangular, circular, oval, opposing semicircles coupled together by parallel lines, or the like. In FIG. 6 (and in other figures), the segmented-electrode-receiving apertures are shown as being rectangular with opposing longitudinal sidewalls 620 coupled to one another by opposing transverse sidewalls 622, where the longitudinal sidewalls 620 extend parallel to the longitudinal length 514 of the electrode carrier 412, and the transverse sidewalls 622 are perpendicular to the longitudinal sidewalls 620 and extend partially around a circumference of the lead body 402/electrode carrier 412.

In at least some embodiments, an inset ledge 624 encircles an opening 626 and provides a surface against which an inner surface (736 in FIG. 7) of the segmented electrode 420 abuts when the segmented electrode 420 is disposed in the segmented-electrode-receiving aperture 518. The ledge 624 can be inset from an outer surface of the electrode carrier 412 any suitable distance. It will be understood that the ledge 624 may be inset from the outer surface of the electrode carrier 412 by a distance that is greater than, equal to, or less than a thickness of the received segmented electrode.

The ledge 624 can extend along all or a portion of a perimeter of the segmented-electrode-receiving aperture 518. In at least some embodiments, the ledge 624 extends each of the longitudinal sidewalls 620 and each of the transverse sidewalls 622. In alternate embodiments, the ledge 624 extends along only one or both of the transverse walls 622, or only one or both of the longitudinal sidewalls 620, or only one of the transverse sidewalls 622 and only one of the longitudinal sidewalls 620. The ledge 624 can extend along all, or only a portion of, any of the sidewalls of the segmented-electrode-receiving aperture 518.

FIG. 7 illustrates, in schematic top view and schematic end view, one embodiment of a segmented electrode 420 suitable for insertion into one of the segmented-electrode-receiving apertures 518. The segmented electrodes can have any suitable shape suitable for use with a corresponding segmented-electrode-receiving aperture including, for example, rectangular, circular, oval, opposing semicircles coupled together by parallel lines, or the like.

In some embodiments the segmented electrode 420 has a length 732 that extends parallel to the longitudinal length 514 of the electrode carrier 412, and a width 734 that is perpendicular to the length 732 and that extends partially around a circumference of the lead body 404/electrode carrier 412. In at least some embodiments, the segmented electrode extends along no more than 75%, 50%, 35%, or 25% of the circumference of the lead body 404/electrode carrier 412. The segmented electrode includes an inner surface 736, an opposing outer stimulation surface 738 through which stimulation energy passes into patient tissue, and sidewalls 739 connecting the inner surface 736 to the outer stimulation surface 738. In at least some embodiments, the outer stimulation surface 738 is arc-shaped.

In at least some embodiments, the segmented electrodes 420 are designed for being pressed into the segmented-electrode-receiving apertures 518 and being retained by an interference fit. The ledge 626 may be used to prevent the segmented electrodes 420 from being pressed through the segmented-electrode-receiving apertures 518 and into the central lumen 510. Additionally, the ledge 626 may be used to reduce, or even prevent, deformation of the segmented electrodes 420 during insertion of the segmented electrodes 420 into their respective segmented-electrode-receiving apertures 518.

In at least some embodiments, one or more coupling grooves, such as coupling groove 740, are defined along one or more perimeter edges of the segmented electrode 420 along, or in proximity to an interface between the outer stimulation surface 738 and one or more of the sidewalls 739. In FIG. 7 (and in other figures), coupling grooves 740 are shown extending along the interface between the outer stimulation surface 738 and the sidewalls 739 that define the length 732 of the segmented electrode 420. It will be understood that the one or more coupling grooves 740 can extend along any number of outer stimulation surface 738 locations along the segmented electrode 420, in any combination, including along an entire perimeter of the outer stimulation surface 738 of the segmented electrode 420.

In at least some embodiments, adhesive is disposed along the one or more coupling grooves 740 after insertion of the segmented electrode into its corresponding segmented-electrode-receiving aperture 518. The adhesive provides additional mechanical support to the interference fit. Additionally, the adhesive facilitates retention of the segmented electrode 420 within the segmented-electrode-receiving aperture 518. Any suitable adhesive may be used including, for example, ultraviolet cure adhesive.

Optionally, one or more anchoring apertures, such as anchoring apertures 742, extend into one or more portions of the segmented electrode 420. Non-conductive material can be disposed in the anchoring apertures 742 and reflowed, or backfilled, or both, to anchor the segmented electrode to the lead. In FIG. 7, anchoring apertures 742 are shown extending completely through the segmented electrode 420 between the outer stimulation surface 738 and the inner surface 736. Any suitable number of anchoring apertures 742 can be formed in the segmented electrodes including, for example, one, two, three, four, five, six, or more anchoring apertures 742. Alternately or additionally, one or more anchoring apertures are defined along one or more sidewalls 739 of the segmented electrode. In at least some embodiments, surface ornamentation (e.g., divots, grooves, scratches, protrusions, nobs, channels, or the like or combinations thereof) is disposed along the inner surface 736 of the segmented electrode to facilitate anchoring of the segmented electrode to the lead.

Turning to FIG. 8, electrodes are typically coupled to terminals (135 in FIG. 1) disposed along a proximal portion of the lead via conductive wires. FIG. 8 illustrates, in schematic perspective view, one embodiment of a conductive wire 844 coupled to the segmented electrode 420. In FIG. 8, the conductive wire 844 is shown coupled to the inner surface 736 of the segmented electrode 420. It will be understood that the conductive wire 844 can be coupled to any surface of the segmented electrode 420 suitable for providing an adequate electrical connection between the conductive wire 844 and the segmented electrode 420 for enabling efficacious stimulation. In at least some embodiments, the segmented electrode 420 defines a conductor groove 848 along the inner surface 736 suitable for receiving, and establishing an electrical connection with, a portion of the conductive wire 844.

FIG. 9 illustrates, in schematic perspective view, one embodiment of one of the segmented electrodes 420 disposed in one of the segmented-electrode-receiving apertures 518 of the electrode carrier 412. As shown in FIG. 9, the segmented electrode 420 is disposed in the segmented-electrode-receiving aperture 518 with the outer stimulation surface 738 of the segmented electrode 420 exposed through the segmented-electrode-receiving aperture 518 and with one of the coupling grooves 740 in proximity to one of the longitudinal sidewalls 620 of the segmented-electrode-receiving aperture 518. In at least some embodiments, adhesive is disposed along the coupling groove 740 to couple the segmented electrode 420 to the electrode carrier 412 via the longitudinal sidewall 620 of the segmented-electrode-receiving aperture 518.

One narrow example of an assembly technique includes: coupling the conductive wires to the segmented electrodes; extending the conductive wires through the segmented-electrode-receiving apertures; disposing the segmented electrodes into the segmented-electrode-receiving apertures; attaching the electrode carrier to the lead body; and coupling the conductive wires to terminals (e.g., terminals 135 of FIG. 1). It will be understood that the above steps can be performed in various different orders.

Optionally, adhesive can be applied along the coupling grooves of the segmented electrodes. Optionally, the electrode carrier (or the interface between the electrode carrier and the lead body, or both) is backfilled with a non-conductive polymer. Optionally, the electrode carrier (or the interface between the electrode carrier and the lead body, or both) is reflowed with a non-conductive polymer. Optionally, the electrode carrier is ground down. In at least some embodiments, the electrode carrier is centerless ground down until the lead and electrode carrier are isodiametric.

Figure 10:
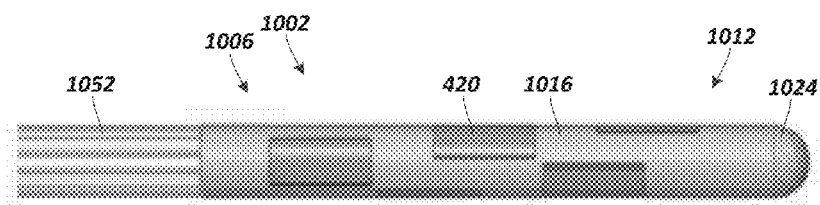
FIG. 10 is a schematic side view of another embodiment of a distal portion of a lead that includes segmented electrodes disposed in an electrode carrier, according to the invention.

Turning to FIG. 10, in at least some embodiments the electrode carrier is adapted for use with a conductor carrier disposed along at least a portion of the lead. FIG. 10 illustrates, in schematic side view, a distal portion 1006 of a lead 1002 that includes an electrode carrier 1012 disposed along, or coupled to, a conductor carrier 1052 of the lead 1002. The electrode carrier 1012 includes a stimulation region 1016 along which multiple segmented electrodes, such as segmented electrode 420, are exposed. Optionally, the electrode carrier 1012 includes a closed distal tip 1024.

Figure 11:
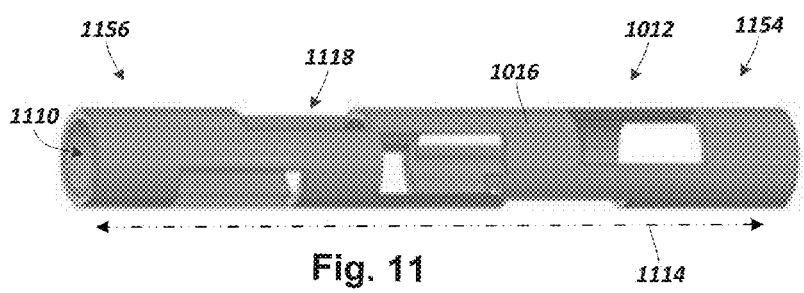
FIG. 11 is a schematic perspective view of one embodiment of the electrode carrier of FIG. 10, according to the invention.

FIG. 11 illustrates, in schematic perspective view, one embodiment of the electrode carrier 1012. In FIG. 11, the electrode carrier 1012 is shown as being cylindrical in shape with a distal portion 1154, an opposing proximal portion 1156, and central lumen 1110 extending along a longitudinal length 1114 of the electrode carrier 1012. Multiple segmented-electrode-receiving apertures 1118 are defined along the electrode carrier 1012.

In at least some embodiments (and as shown in FIG. 11), the electrode carrier 1012 does not include an inset ledge disposed along a perimeter of the segmented-electrode-receiving apertures 1118. In at least some embodiments, the conductor carrier is at least partially received by the central lumen 1110 of the electrode carrier 1012 and prevents the segmented electrodes 420 from being pressed through the segmented-electrode-receiving apertures 1118 and into the central lumen 1110. Additionally, the conductor carrier may be used to reduce, or even prevent, deformation of the segmented electrodes 420 during insertion of the segmented electrodes 420 into their respective segmented-electrode-receiving apertures 1118.

Figure 12:
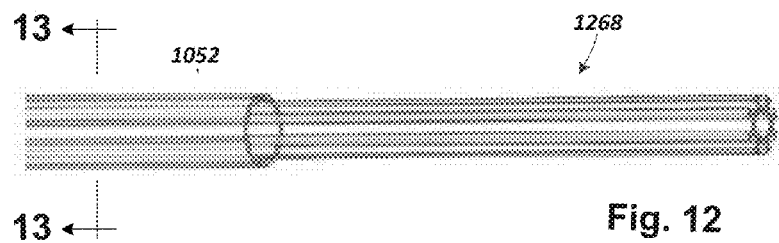
FIG. 12 is a schematic perspective view of one embodiment of a conductor carrier coupleable to the electrode carrier of FIG. 10, according to the invention.
Figure 13:
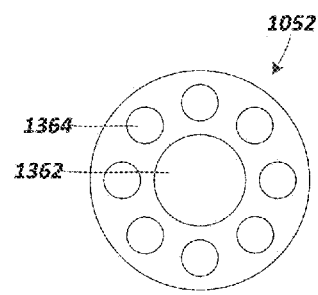
FIG. 13 is a schematic transverse cross-sectional view of one embodiment of the conductor carrier of FIG. 12, according to the invention.

Turning to FIG. 12, in at least some embodiments the conductor carrier includes conductor lumens for housing conductive wires. FIG. 12 illustrates, in schematic perspective view, one embodiment of a distal portion of the conductor carrier 1052. FIG. 13 illustrates, in schematic transverse cross-sectional view, one embodiment of the conductor carrier 1052. The conductor carrier 1052 defines a central lumen 1362 and one or more conductor lumens 1364 defined along the conductor carrier 1052 peripheral to the central lumen 1362. The one or more conductor lumens 1364 can be adapted to receive any suitable number of conductive wires including, for example, one, two, three, four, five, six, seven, eight, or more conductive wires. In FIGS. 12 and 13, the conductor lumens 1364 are shown adapted to each receive a single conductive wire. It will be understood that, in alternate embodiments, the conductor carrier does not define any conductor lumens and the conductors extend along the central lumen 1362.

FIG. 12 shows an ablated region 1268 defined along the distal portion of the conductor carrier 1052. An outer portion of the conductor carrier 1052 is removed along a length of the ablated region 1268 to expose the conductor lumens 1364 to the segmented-electrode-receiving apertures 1118 when the conductor carrier 1052 is received by the central lumen 1110 of the electrode carrier 1012. In at least some embodiments, the ablated region 1268 extends around an entire circumference of the conductor carrier 1052. Thus, the conductive wires can be attached at one end to the segmented electrodes, extended through a segmented-electrode-receiving aperture 1118, and further extended along conductor lumens to a proximal portion of the lead.

Figure 14:
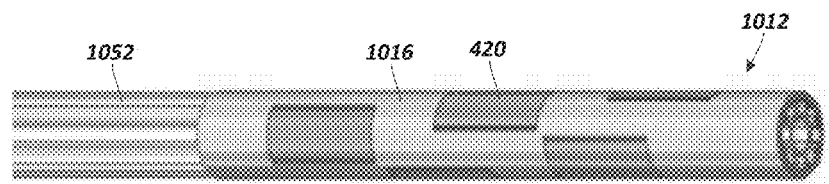
FIG. 14 is a schematic perspective view of one embodiment of the electrode carrier of FIG. 11 disposed along the conductor carrier of FIG. 12, according to the invention.
Figure 15:
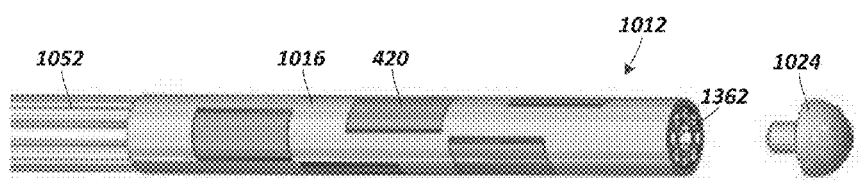
FIG. 15 is a schematic perspective view of one embodiment of the electrode carrier of FIG. 11 disposed along, or coupled to, the conductor carrier of FIG. 12 and a distal tip suitable for coupling to the electrode carrier via partial insertion of the distal tip into a central lumen of the conductor carrier, according to the invention.

FIG. 14 illustrates, in schematic perspective view, one embodiment of the ablated region 1268 of the conductor carrier 1052 disposed in the central lumen of the electrode carrier 1012. It will be understood that the length of the ablated region 1268 can be greater than, less than, or equal to the longitudinal length 1114 of the electrode carrier. In FIG. 14, the ablated region 1268 is shown having a length that is equal to the longitudinal length 1114 of the electrode carrier 1012. It may be advantageous for the length of the ablated region 1268 to be equal to the longitudinal length 1114 of the electrode carrier 1012 to facilitate attachment of the distal tip 1024 to the distal portion 1154 of the electrode carrier 1012 via insertion of a portion of the distal tip 1024 into a distal end of the central lumen 1362 of the conductor carrier 1052, as shown in FIG. 15.

Figure 16:
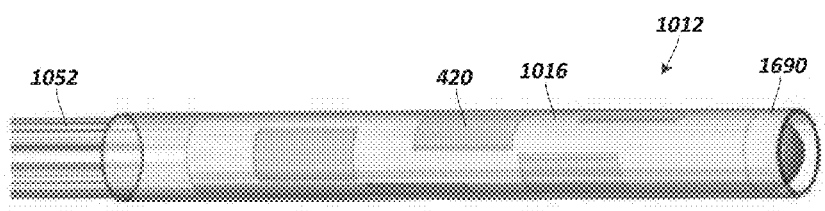
FIG. 16 is a schematic perspective view of one embodiment of heat shrink tubing disposed over the electrode carrier of FIG. 11, according to the invention.

Turning to FIG. 16, in at least some embodiments heat shrink tubing is disposed over the segmented electrodes to facilitate retention of the segmented electrodes in the segmented-electrode-receiving apertures. FIG. 16 illustrates, in schematic perspective view, one embodiment of heat shrink tubing 1690 disposed over the segmented electrodes 420, the electrode carrier 1012, and at least a portion of the conductor carrier 1052.

In at least some embodiments, non-conductive material is reflowed (or backfilled) to facilitate coupling of the electrode carrier, the electrodes, or both, to the lead. Backfilling typically involves injecting non-conductive material into the region of interest and allowing the introduced material to cure. Reflowing involves creating enough flow (e.g., by application of heat) of non-conductive material to cause the material to flow into gaps and to cure. The non-conductive material may be material from the lead body, electrode carrier, or the like. Alternately or additionally, the non-conductive material may be from an additional material, such as a polymer tube, that is disposed in proximity to the region of interest and heated to induce flow.

When heat shrink tubing is used, a polymer tube (not shown) for reflowing may be disposed between the segmented electrodes 420 and the heat shrink tubing 1690. It will be understood that the heat shrink tubing can, optionally, be used in conjunction with any of the disclosed embodiments of the electrode carrier. Additionally, it will be understood that disposing a polymer tube for reflowing between the segmented electrodes 420 and the heat shrink tubing 1690 can also be used in conjunction with any of the disclosed embodiments of the electrode carrier.

One narrow example of an assembly technique with a conductor carrier includes: inserting a portion of the conductor carrier into the central lumen of the electrode carrier; coupling the conductive wires to the segmented electrodes; extending the conductive wires through the segmented-electrode-receiving apertures and along the conductor carrier; disposing the segmented electrodes into the segmented-electrode-receiving apertures; attaching the electrode carrier to the lead body; and coupling the conductive wires to terminals (e.g., terminals 135 of FIG. 1). It will be understood that the above steps can be performed in various different orders.

Optionally, one end of the conductor carrier is ablated. Optionally, the distal tip is coupled to the distal portion of the electrode carrier. Optionally, the electrode carrier (or the interface between the electrode carrier and the conductor carrier, or both) is backfilled with a non-conductive polymer. Optionally, the electrode carrier (or the interface between the electrode carrier and the conductor carrier, or both) is reflowed with a polymeric polymer. Optionally, heat shrink tubing is disposed over the segmented electrodes. Optionally, the electrode carrier is ground down. In at least some embodiments, the electrode carrier is ground down until the lead and electrode carrier are isodiametric.

Figure 17A:
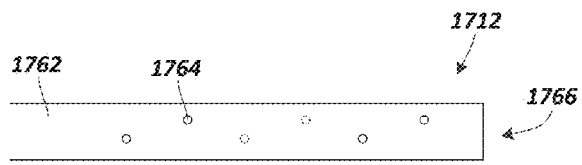
FIG. 17A is a schematic side view of one embodiment of an inner sleeve of an electrode carrier, according to the invention.

Turning to FIG. 17A, in at least some embodiments the electrode carrier includes multiple concentric sleeves. FIG. 17A illustrates, in schematic side view, one embodiment of an inner sleeve 1762 of an electrode carrier 1752. The inner sleeve 1762 defines a central lumen 1766 and a plurality of conductor apertures, such as conductor aperture 1764, extending along a sidewall of the electrode carrier 1752 between an outer surface of the inner sleeve 172 and the central lumen 1766.

Figure 17B:
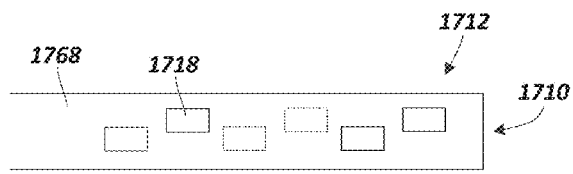
FIG. 17B is a schematic side view of one embodiment of an outer sleeve of an electrode carrier, according to the invention.

FIG. 17B illustrates, in schematic side view, one embodiment of an outer sleeve 1766 of an electrode carrier 1752. The outer sleeve 172 defines a central lumen 1710 and a plurality of segmented-electrode-receiving apertures, such as segmented-electrode-receiving aperture 1718, extending between an outer surface of the outer sleeve 1768 and the central lumen 1710.

Figure 17C:
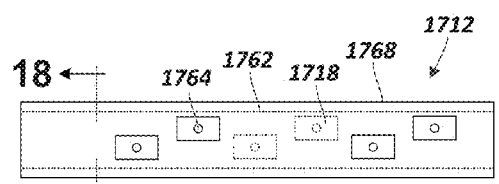
FIG. 17C is a schematic side view of another embodiment of an electrode carrier that includes the outer sleeve of FIG. 17B disposed over the inner sleeve of FIG. 17A, according to the invention.
Figure 18:
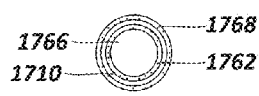
FIG. 18 is a schematic transverse cross-sectional view of one embodiment of the electrode carrier of FIG. 17C, according to the invention.

FIG. 17C illustrates, in schematic side view, one embodiment of the inner sleeve 1762 disposed in the central lumen 1710 of the outer sleeve 1768. FIG. 18 illustrates, in schematic transverse cross-sectional view, one embodiment of the inner sleeve 1762 disposed in the central lumen 1710 of the outer sleeve 1768. The conductor apertures 1764 are aligned with the segmented-electrode-receiving apertures 1718 such that, when a segmented electrode is disposed in one of the segmented-electrode-receiving apertures 1718, a conductor extending along the central lumen 1766 can be extended through one of the conductor apertures 1764 and couple with the segmented electrode. In at least some embodiments, the conductor apertures 1764 and the segmented-electrode-receiving apertures 1718 are each configured into similar patterns such that each of the conductor apertures 1764 can be concurrently aligned with a different segmented-electrode-receiving aperture 1718.

Figure 19:
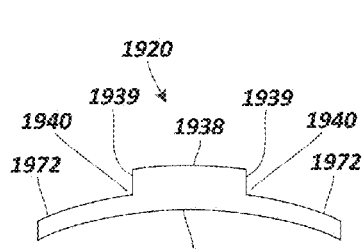
FIG. 19 is a schematic end view of another embodiment of a segmented electrode having anchoring tabs, according to the invention.
Figure 20:
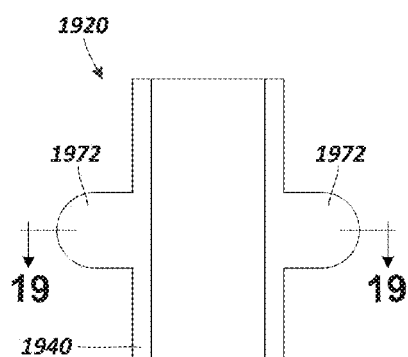
FIG. 20 is a schematic top view of one embodiment of the segmented electrode of FIG. 19, according to the invention.

Turning to FIG. 19, in at least some embodiments the segmented electrodes include anchoring units for facilitating anchoring of the segmented electrodes to the lead. FIG. 19 illustrates, in schematic end view, another embodiment of a segmented electrode 1920 suitable for use with any of the disclosed embodiments of the electrode carrier. FIG. 20 illustrates, in schematic top view, one embodiment of the segmented electrode 1920. The segmented electrode includes an inner surface 1936, an opposing outer surface 1938 through which stimulation energy passes into patient tissue, and sidewalls 1939 connecting the inner surface 1936 to the outer stimulation surface 1938. In at least some embodiments, the outer stimulation surface 1938 is arc-shaped. Anchoring tabs 1972 extend from one or more of the sidewalls 1939 of the segmented electrode 1920. The segmented electrode 1920 may include any suitable number of anchoring tabs. In FIGS. 19 and 20, the anchoring tabs 1972 are shown extending along the opposing longitudinal sidewalls 1939 of the segmented electrodes 420. Each individual anchoring tab 1972 can extend around any suitable portion of a circumference of lead (e.g., at least 10%, 15%, 20%, 25%, or more of the circumference).

In at least some embodiments, one or more coupling grooves, such as coupling groove 1940, are defined along one or more perimeter edges of the outer stimulation surface 1938 of the segmented electrode 1920. In FIGS. 19 and 20, the coupling grooves 1940 are shown extending along the same opposing edges of the segmented electrodes 1920 as the anchoring tabs 1972.

Figure 21A:
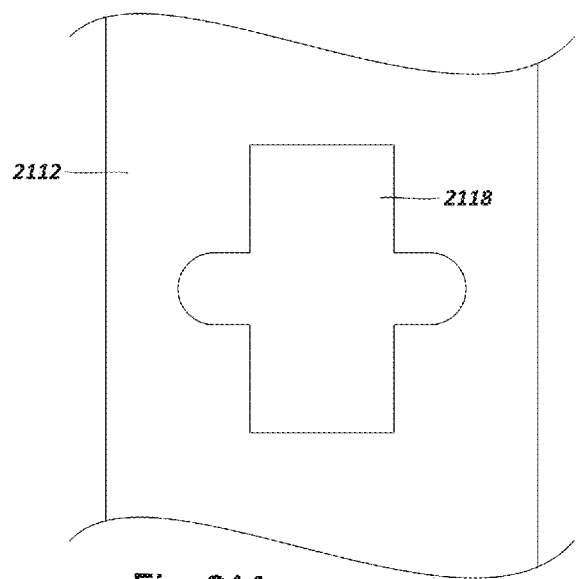
FIG. 21A is a schematic top view of one embodiment of an electrode carrier having segmented-electrode-receiving apertures suitable for receiving the segmented electrode and corresponding anchoring tabs of FIGS. 19 and 20, according to the invention.

In at least some embodiments, the electrode carrier defines segmented-electrode-receiving apertures adapted to receive the segmented electrodes and their anchoring tabs 1972. FIG. 21A illustrates, in schematic top view, one embodiment of an electrode carrier 2112 that defines a segmented-electrode-receiving aperture 2118 having a shape that corresponds to the shape of the segmented electrode 1920 and corresponding anchoring tab(s) 1972.

Figure 21B:
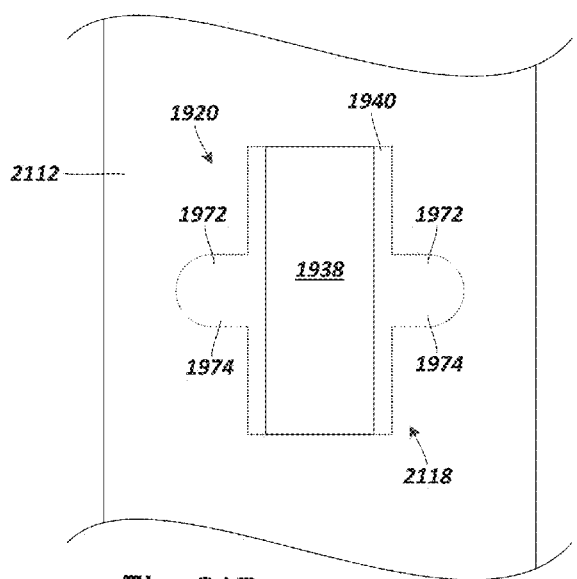
FIG. 21B is a schematic top view of one embodiment of the segmented electrode and corresponding anchoring tabs of FIGS. 19 and 20 disposed along a portion of the electrode carrier of FIG. 21A with the anchoring tabs covered in non-conductive polymer, according to the invention.

FIG. 21B illustrates, in schematic top view, one embodiment of the segmented electrode 1920 disposed in the segmented-electrode-receiving aperture 2118. In FIG. 21B, the anchoring tabs 1972 and the coupling grooves 1940 of the segmented electrode 1920 are shown covered in non-conductive material 1974 (from reflowing, backfilling, or both) to anchor the segmented electrode to the lead. The outer stimulation surface 1938 of the segmented electrode 1920 is exposed through the non-conductive material 1974 and the segmented-electrode-receiving apertur 2118.

In at least some embodiments, an assembly technique for segmented electrodes with anchoring tabs includes: inserting the segmented electrodes 1920 and corresponding anchoring tabs 1972 into the segmented-electrode-receiving apertures 2118; and reflowing, the electrode carrier (e.g., using a non-conductive polymer from the lead, the electrode carrier, or a polymer tube disposed over the electrode carrier) or, alternately (or additionally) backfilling the electrode carrier (e.g., using a non-conductive polymer) to couple the segmented electrode 1920 to the lead.

Figure 22:
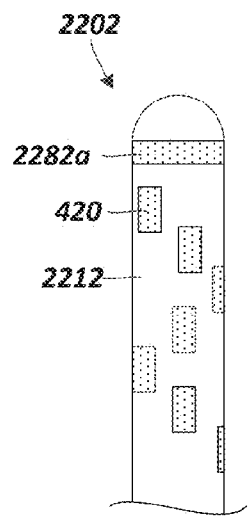
FIG. 22 is a schematic side view of one embodiment of multiple electrodes disposed along a lead, the multiple electrodes including multiple segmented electrodes and a ring electrode distal to the segmented electrodes, according to the invention.

Turning to FIG. 22, the segmented electrodes can be disposed along the distal portion of the lead in any suitable configuration. Any suitable total number of electrodes may be used. It may be advantageous to use eight electrodes (as shown in each of FIGS. 22-25) to facilitate use of the leads with control modules and connectors adapted for use with lead having eight electrodes. In at least some embodiments, the segmented electrodes are used in conjunction with one or more ring electrodes, a tip electrode, or one or more ring electrodes and a tip electrode. In at least some embodiments, the total number of electrodes includes seven segmented electrodes and either a tip electrode or a ring electrode. When the segmented electrodes are used in conjunction with one or more ring electrodes, the one or more ring electrodes can be proximal to at least one of the segmented electrodes, distal to at least one of segmented electrodes, or both.

Figure 23:
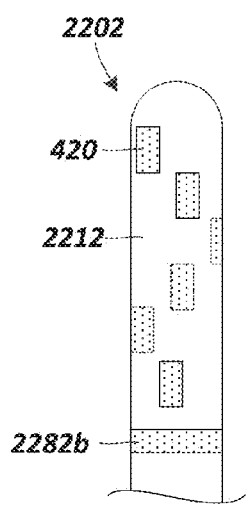
FIG. 23 is a schematic side view of one embodiment of multiple electrodes disposed along a lead, the multiple electrodes including multiple segmented electrodes and a ring electrode proximal to the segmented electrodes, according to the invention.
Figure 24:
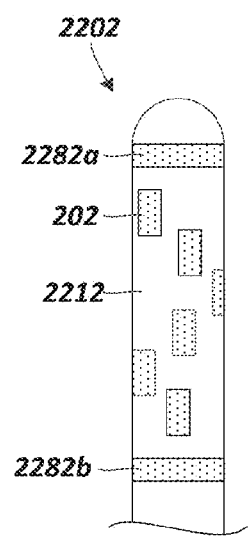
FIG. 24 is a schematic side view of one embodiment of multiple electrodes disposed along a lead, the multiple electrodes including multiple segmented electrodes, a ring electrode distal to the segmented electrodes, and another ring electrode proximal to the segmented electrodes, according to the invention.
Figure 25:
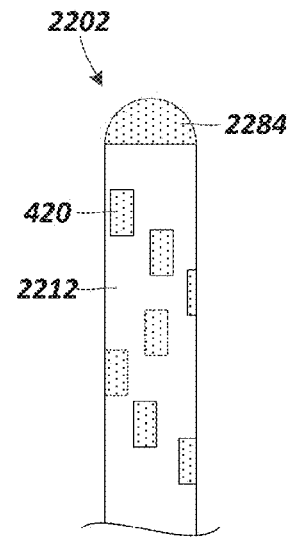
FIG. 25 is a schematic side view of one embodiment of multiple electrodes disposed along a lead, the multiple electrodes including multiple segmented electrodes and a tip electrode distal to the segmented electrodes, according, to the invention.

FIG. 22 illustrates, in schematic side view, one embodiment of multiple segmented electrodes 420 disposed along a lead 2202 and extending through an electrode carrier 2212. A ring electrode 2282a is disposed distal to the segmented electrodes 420. FIG. 23 illustrates, in schematic side view, one embodiment of multiple segmented electrodes 420 disposed along the lead 402 and extending through the electrode carrier 412. A ring electrode 2282b is disposed proximal to the segmented electrodes 420. FIG. 24 illustrates, in schematic side view, one embodiment of multiple segmented electrodes 420 disposed along the lead 402 and extending through the electrode carrier 412. A first ring electrode 2282a is disposed distal to the segmented electrodes 420 and a second ring electrode 2282b is disposed proximal to the segmented electrodes 420. FIG. 25 illustrates, in schematic side view, one embodiment of multiple segmented electrodes 420 disposed along the lead 402 and extending through the electrode carrier 412. A tip electrode 2284 is disposed distal to the segmented electrodes 420. It will be understood that one or more of the segmented electrodes shown in FIGS. 22-25 may include anchoring tabs.

One narrow example of an assembly technique with a tip electrode, one or more ring electrode, or both, includes: coupling the conductive wires to the electrodes; extending the conductive wires through the segmented-electrode-receiving apertures; coupling the ring electrode(s), tip electrode, or both, to the lead; disposing the segmented electrodes into the segmented-electrode-receiving apertures; attaching the electrode carrier to the lead; and coupling the conductive wires to terminals (e.g., terminals 135 of FIG. 1).

It will be understood that the above steps can be performed in various different orders. In at least some embodiments, when the ring electrode is disposed proximal to the segmented electrodes, the ring electrode is coupled to the lead prior to coupling the electrode carrier to the lead. In at least some embodiments, when the ring electrode is disposed distal to the segmented electrodes, the ring electrode is coupled to the lead after coupling the electrode carrier to the lead. In at least some embodiments, the tip electrode is coupled to the lead after coupling the electrode carrier to the lead.

Optionally, adhesive can be applied along the coupling grooves of the segmented electrodes. Optionally, the electrode carrier (or the interface between the electrode carrier and the lead body, or both) is backfilled with a non-conductive polymer. Optionally, the electrode carrier (or the interface between the electrode carrier and the lead body, or both) is reflowed with a non-conductive polymer. Optionally, the electrode carrier is ground down. In at least some embodiments, the electrode carrier is ground down until the lead and electrode carrier are isodiametric.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation lead, comprising:
   a lead body comprising a longitudinal length, a distal portion, and a proximal portion;
   a plurality of terminals disposed along the proximal portion of the lead body;
   an electrode carrier coupled to, or disposed along, the distal portion of the lead body, the electrode carrier having an outer surface, the electrode carrier comprising
      a central lumen, and
      a stimulation region defining a plurality of segmented-electrode-receiving apertures extending between the outer surface and the central lumen, wherein the stimulation region is formed of a non-conductive material, and wherein, for each of the segmented-electrode-receiving apertures, a ledge is disposed around a perimeter of that segmented-electrode-receiving aperture, the ledge inset from the outer surface of the electrode carrier;
   a plurality of electrodes comprising a plurality of segmented electrodes each having an outer stimulation surface, an opposing inner surface, and sidewalls connecting the outer stimulation surface to the inner surface, each of the segmented electrodes extending around no more than 75% of a circumference of the lead, each of the segmented electrodes disposed in a different one of the segmented-electrode-receiving apertures of the electrode carrier with the outer stimulation surface exposed through the segmented-electrode-receiving aperture and the inner surface abutting the ledge disposed around the perimeter of that segmented-electrode-receiving aperture; and
   a plurality of conductive wires extending along the lead body and coupling the plurality of electrodes to the plurality of terminals.

2. The lead of claim 1, further comprising a conductor carrier disposed along the central lumen of the electrode carrier, the conductor carrier defining a central lumen, the conductor carrier housing portions of each of the plurality of conductive wires.

3. The lead of claim 2, wherein the conductor carrier defines a plurality of conductor lumens disposed peripherally about the central lumen of the conductor carrier, and wherein the plurality of conductive wires are disposed in the plurality of conductor lumens.

4. The lead of claim 3, wherein the conductor carrier defines an ablated region exposing each of the plurality of conductor lumens to the plurality of segmented-electrode-receiving apertures.

5. The lead of claim 1, wherein the electrode carrier comprises an inner sleeve and an outer sleeve disposed over the inner sleeve, the outer sleeve defining the plurality of segmented-electrode-receiving apertures and the inner sleeve defining a plurality of conductor apertures exposing the central lumen of the electrode carrier to the plurality of segmented-electrode-receiving apertures defined in the outer sleeve, wherein the conductor apertures are smaller than the segmented-electrode-receiving apertures.

6. The lead of claim 1, wherein the outer stimulation surfaces of the plurality of segmented electrodes are arc-shaped.

7. The lead of claim 1, wherein at least one of the plurality of segmented electrodes defines at least one coupling groove disposed along the outer stimulation surface of the segmented electrode, the at least one coupling groove attached to the stimulation region of the electrode carrier via adhesive.

8. The lead of claim 1, wherein at least one of the segmented electrodes defines at least one anchoring aperture extending between the outer stimulation surface and the inner surface of the segmented electrode, the at least one anchoring aperture filled with polymeric material.

9. The lead of claim 1, wherein at least one of the plurality of segmented electrodes comprises at least one anchoring tab extending outwardly from at least one of the sidewalls of the segmented electrode.

10. The lead of claim 1, wherein the plurality of electrodes further comprises at least one of a tip electrode or at least one ring electrode.

11. An electrical stimulating system comprising:
    the lead of claim 1;
    a control module electrically coupled to the plurality of electrodes of the lead, the control module comprising
       a housing, and
       an electronic subassembly disposed in the housing; and
    a connector assembly for receiving the lead, the connector assembly comprising
       a connector housing defining at least one port configured and arranged for receiving the lead, and
       a plurality of connector contacts disposed in the connector housing and configured and arranged to couple to the plurality of terminals disposed along the proximal portion of the lead body.

* * * * *